United States Patent [19]
Hetzler et al.

[11] Patent Number: 5,910,136
[45] Date of Patent: Jun. 8, 1999

[54] ORIENTED POLYMERIC MICROPOROUS FILMS WITH FLEXIBLE POLYOLEFINS

[75] Inventors: Kevin G. Hetzler, Alpharetta; Rob L. Jacobs, Woodstock, both of Ga.

[73] Assignee: Kimberly-Clark Worldwide, Inc., Neenah, Wis.

[21] Appl. No.: 08/775,087

[22] Filed: Dec. 30, 1996

[51] Int. Cl.$^6$ .............................. A61F 13/15; A61F 13/20
[52] U.S. Cl. ............................................. 604/367; 525/191
[58] Field of Search .......................... 604/367; 521/143; 525/95, 191; 524/427; 429/250

[56] References Cited

U.S. PATENT DOCUMENTS

| | | |
|---|---|---|
| 3,338,992 | 8/1967 | Kinney . |
| 3,426,754 | 2/1969 | Bierenbaum et al. . |
| 3,502,538 | 3/1970 | Petersen . |
| 3,679,538 | 7/1972 | Druin et al. . |
| 3,843,761 | 10/1974 | Bierenbaum et al. . |
| 3,844,865 | 10/1974 | Elton et al. . |
| 3,932,682 | 1/1976 | Loft et al. . |
| 4,105,737 | 8/1978 | Suzuki . |
| 4,138,459 | 2/1979 | Branzinsky et al. . |
| 4,166,464 | 9/1979 | Korpman ................................. 128/287 |
| 4,257,997 | 3/1981 | Soehngen et al. . |
| 4,340,563 | 7/1982 | Appel et al. . |
| 4,519,909 | 5/1985 | Castro . |
| 4,539,256 | 9/1985 | Shipman . |
| 4,613,643 | 9/1986 | Nakamura et al. ..................... 524/426 |
| 4,668,566 | 5/1987 | Braun . |
| 4,726,989 | 2/1988 | Mrozinski . |
| 4,801,494 | 1/1989 | Datta et al. . |
| 4,906,513 | 3/1990 | Kebbell et al. . |
| 4,921,652 | 5/1990 | Tsuji et al. . |
| 4,923,650 | 5/1990 | Antoon, Jr. et al. . |
| 4,994,335 | 2/1991 | Kamaei et al. . |
| 5,008,296 | 4/1991 | Antoon, Jr. et al. . |
| 5,073,316 | 12/1991 | Bizen et al. . |
| 5,169,712 | 12/1992 | Tapp . |
| 5,173,235 | 12/1992 | Kamei et al. . |
| 5,176,953 | 1/1993 | Jacoby et al. . |
| 5,244,482 | 9/1993 | Hassenboehler, Jr. et al. . |
| 5,258,156 | 11/1993 | Kurauchi et al. . |
| 5,467,765 | 11/1995 | Maturaporn . |
| 5,468,807 | 11/1995 | Tsurutani et al. . |
| 5,492,751 | 2/1996 | Butt, Sr. et al. . |
| 5,522,810 | 6/1996 | Allen, Jr. et al. ....................... 604/366 |
| 5,543,206 | 8/1996 | Austin et al. . |

FOREIGN PATENT DOCUMENTS

| | | |
|---|---|---|
| 0 214 859 A2 | 3/1987 | European Pat. Off. . |
| 0 434 115 A1 | 6/1991 | European Pat. Off. . |
| 0 444 671 A3 | 9/1991 | European Pat. Off. . |
| 0 554 896 A1 | 8/1993 | European Pat. Off. . |
| 0 605 831 A1 | 7/1994 | European Pat. Off. . |
| WO 96/19346 | 6/1996 | WIPO . |

*Primary Examiner*—Mark O. Polutta
*Assistant Examiner*—Ki Yong O
*Attorney, Agent, or Firm*—Brinks Hofer Gilson & Lione

[57] ABSTRACT

The present invention relates to a microporous film including a flexible polyolefin, more particularly, a propylene-based polymer with atactic polypropylene units. The present invention is also directed to a method of making the microporous film.

12 Claims, 2 Drawing Sheets

ORIENTED POLYMERIC MICROPOROUS FILMS WITH FLEXIBLE POLYOLEFINS

FIELD OF INVENTION

The present invention is directed to oriented microporous thermoplastic films utilizing flexible polyolefins, more specifically, propylene-based polymers including atactic polypropylene units in the polymer chain. In addition, the present invention is directed to a method of making such films.

BACKGROUND OF THE INVENTION

The present invention is directed to microporous thermoplastic films. Such materials have a wide variety of uses, especially in the areas of limited use and disposable items.

Films have been traditionally used to provide barrier properties in limited use or disposable items. By limited use or disposable, it is meant that the product and/or component is used only a small number of times or possibly only once before being discarded. Examples of such products include, but are not limited to, surgical and health care related products such as surgical drapes and gowns, disposable work wear such as coveralls and lab coats and personal care absorbent products such as diapers, training pants, incontinence garments, sanitary napkins, bandages, wipes and the like. In personal care absorbent products such as infant diapers and adult incontinence products, films are used as the outer covers with the purpose of preventing body wastes from contaminating the clothing, bedding and other aspects of the surrounding environment of use. In the area of protective apparel including hospital gowns, films are used to prevent cross exchange of microorganisms between the wearer and the reduced noise patient.

While these films can be effective barriers, they are not aesthetically pleasing because their surfaces are smooth and either feel slick or tacky. They are also visually flat and "plasticy" and make a great deal of noise as a result of user's movement thereby making them less desirable in apparel applications and other uses where they are in contact with human skin. It would be more preferable if these items were more cloth-like from both a tactile and visual standpoint. For example, infant diapers that have the feel and appearance of traditional cloth undergarments are perceived as premium products and may, in some cases, overcome the tendency to believe that they need to be covered by outer garments for aesthetic reasons. Garment-like adult incontinence products could improve the self-image of the incontinent individual. In addition, more garment-like isolation gowns would help the hospital environment feel less foreign and threatening to the patient and increase the comfort of the wearer. It is also preferable to have films that can make an outercover material with more elastic give and recovery to provide better fit and comfort.

Lamination of films have been used to create materials which are both impervious to liquids and somewhat cloth-like in appearance and texture. The outer covers on disposable diapers are but one example. In this regard, reference may be had to coassigned U.S. Pat. No. 4,818,600 dated Apr. 4, 1989 and U.S. Pat. No. 4,725,473 dated Feb. 16, 1988. Surgical gowns and drapes are other examples. See, in this regard, coassigned U.S. Pat. No. 4,379,102 dated Apr. 5, 1983.

A primary purpose of the film in such laminations is to provide barrier properties. There is also a need for such laminates to be breathable so that they have the ability to transmit moisture vapor. Apparel made from laminations of these breathable or microporous films are more comfortable to wear by reducing the moisture vapor concentration and the consequent skin hydration underneath the apparel item.

The conventional process for obtaining a breathable microporous film has been to stretch a thermoplastic film containing filler. Microvoids are created by the filler particles during the stretching process. The film is usually heated prior to these drawing processes to make the film more plastic or malleable. Generally, the amount of stretch on a film is expressed in "draw ratio," the ratio of the film wind-up or take-up speed to the speed of the film issuing from the extrusion die or from roll and winding.

A film can be stretched in the machine-direction, the cross-machine direction or both. Stretching the film in the cross direction is particularly challenging because forces must be applied to the edges of the film to cause it to elongate. Tenter frames are commonly used. In contrast, stretching the film in the machine direction is relatively easy. It is only necessary to increase the draw, or speed ratio, between two rollers while the film is in the heated or plastic state. There is a durability problem, however, with uni-directionally-stretched films, be it machine direction or cross-direction. Uni-directional stretching causes molecular orientation only in the stretched direction. This results in films that are easily torn or split along that dimension. For example, a machine-directionally oriented film has a propensity to split or tear along the machine direction. Also, the tensile characteristics of the film are dramatically increased in the machine direction, but the tensile strength in the cross-direction is significantly inferior to that of the machine direction.

Moreover, a greater desired breathability generally requires greater filler content in the film and greater draw ratio. However, a high filler content and large draw ratio reduces the strength properties of the stretched film, such as transverse or cross-machine direction strain and elongation values. As a result an increased thickness is generally required to compensate. This increased film thickness increases the cost of the film.

There is therefore a need for a low-gauge, microporous film and nonwoven laminate using materials and processes that provides a product with both the cloth-like aesthetics and the in-use durability that are desired.

SUMMARY OF THE INVENTION

The present invention relates to an oriented microporous film comprising microporous oriented film comprising a polyolefin resin including a propylene-based polymer with atactic polypropylene units and at least about 40% by weight of the film is a filler, wherein the filler includes particles having a particle size that contributes to pore formation.

In one embodiment, polypropylene-based polymer has a crystallinity level of from about 5 to about 30% by weight of said polymer, measured by the second heat of the differential scanning calorimetry method.

The preferred film product of the present invention has a water vapor transmission rate of at least about 300 g/m$^2$/24 hours, measured by test procedure modified ASTM Test Method E 96-80. In one application, the more preferred film has a water vapor transmission rate of from about 1,200 to 2,200 g/m$^2$/24 hours. In another application, the more preferred film has a water vapor transmission rate of at least about 3,500 g/m$^2$/24 hours.

The present invention also relates to a method of preparing a microporous polymeric film with flexible polyolefins. The method includes preparing a polyolefin resin including a propylene-based polymer containing atactic polypropylene units, preparing a filled resin by adding at least about 50% by weight of the film of a filler to said polyolefin resin, said filler including a plurality of solid particles having a particle size that contributes to pore formation, preparing a film from said filled resin and orienting said film. In one embodiment, the film is oriented by applying a draw ratio of at least about 3:1 on the film. In another embodiment, the film may be oriented by cold stretching.

The film of the present invention can be incorporated into a laminate wherein a support layer is preferably adhesive- or point-bonded to the film. Because the preferred film of the present invention can be oriented with a relatively low draw ratio, the oriented film has superior transverse (or cross-machine direction) strain properties and transverse direction stress values. Moreover, the preferred film of the present invention has a higher water vapor transmission rate at lower draw ratios when coMPared to film made from materials having higher crystallinity. As a result of the lower draw ratio, the preferred film of the present invention is more durable and has a more balanced tensile strength in the MD and CD directions.

Such films have a wide variety of uses including, but not limited to, applications in personal care absorbent articles including diapers, training pants, sanitary napkins, incontinence devices, bandages and the like. These same films also may be used in items such as surgical drapes and gowns as well as various articles of clothing either as the entire article or simply as a component thereof.

DETAILED DESCRIPTION OF THE PREFERRED EMBODIMENTS

Figure 1:
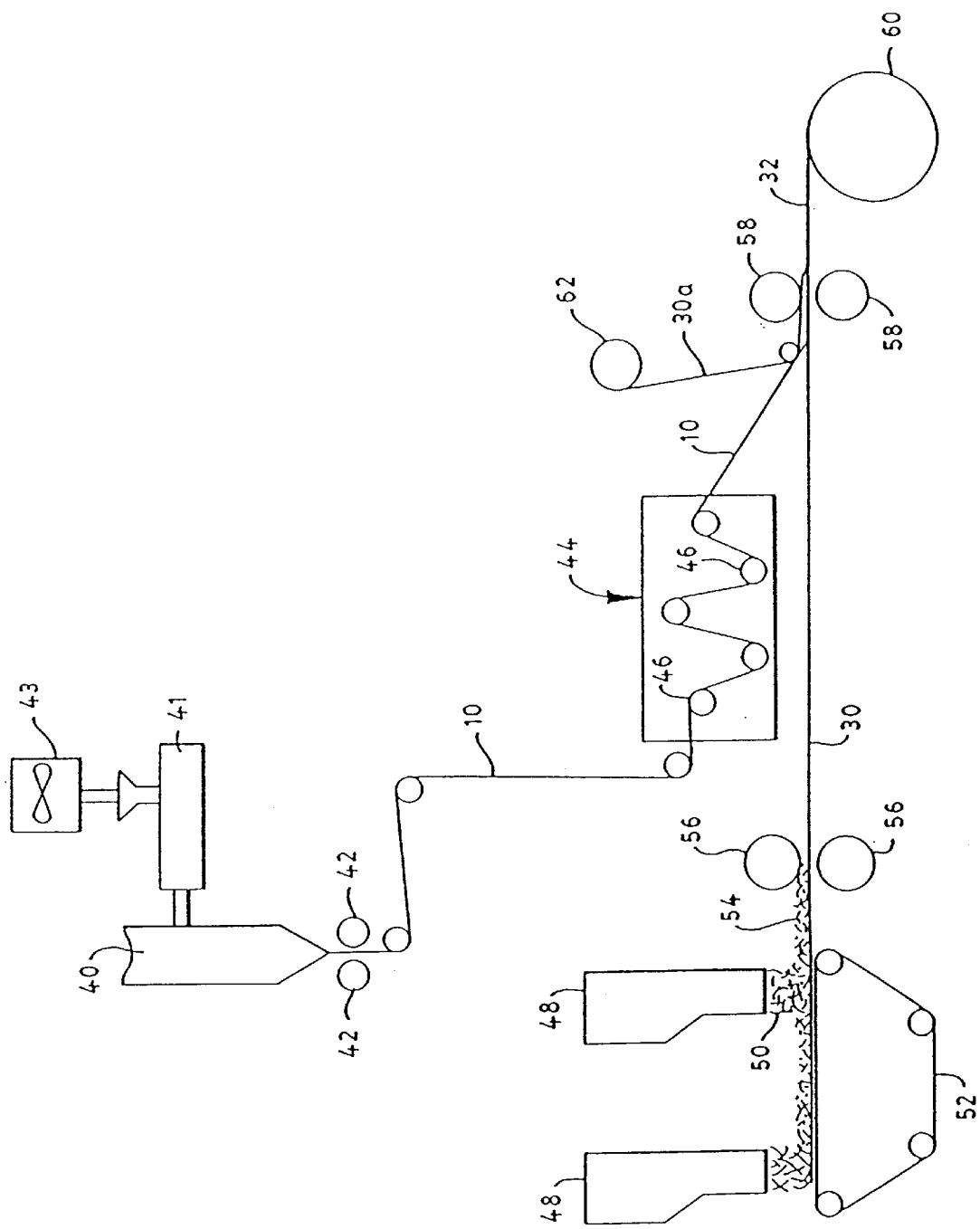
FIG. 1 is a schematic side view of a process for forming a film and laminate according to the present invention

The present invention is directed to breathable film that includes at least one flexible polyolefin in the polyolefin resin.

The term "flexible polyolefins" as used herein includes those polymer materials that are flexible film- or fiber-forming materials that are nonelastomers. Such materials show some elastomeric-type properties (i.e., flexibility, iMPact resistance, some limited elasticity, ability to swell in solvents, etc.), but their main characteristic is a combination of flexibility and dimension flexibility. These materials maintain a high melting point, a property unique in polyolefins.

More particularly, flexible polyolefins are propylene-based polymers having atactic polypropylene units in the polymer chain. For example, the propylene-based polymer may be isotactic polypropylene with atactic groups incorporated within the main polymer chain to break up the crystallinity. Alternatively, it could be an "in-situ" blend of atactic and isotactic polypropylene. Preferably, the propylene-based polymer has a controlled crystallinity of the resulting crystallinity value (in touler/grams)from about 10–30%, as determined by differential scanning calorimetry (DSC). As used herein, "DSC" method determines the crystallinity by integrating the area on a DSC second heat scan and dividing by 185 Joules per gram, the approximate crystallinity of pure polypropylene available from Shell Chemical CoMPany of Houston, Tex.

Suitable flexible polyolefin include those designated by the brand name RexFlex™ FPO, available from Rexene Corporation of Dallas, Tex. The RexFlex™ FPO polymers include homopolymers as well as copolymer wherein the comonomer is ethylene.

The polyolefin resin may also include other polymeric materials, so long as these additional materials do not adversely effect the advantages of the present invention. These additional polymeric materials include, for example, low crystallinity random polypropylene copolymers (RCPs) with less than about 30% crystallinity as determined by DSC such as Shell 6D82 brand copolymers, available from Shell Chemical CoMPany, Houston, Tex. More preferably, the polyolefin resin of the present invention includes a blend of from about 10 to about 80% flexible polyolefin and up to about 75% RCP. Preferably, the RCP used in the present invention has an ethylene content of at least 3% by weight.

The polyolefin resin may optionally include an elastomeric material. Elastomeric thermoplastic polymers useful in the practice of this invention may be those made from block copolymers such as polyurethanes, copolyether esters, polyamide polyether block copolymers, ethylene vinyl acetates (EVA), block copolymers having the general formula A-B-A' or A-B like copoly(styrene/ethylene-butylene), styrene-poly(ethylene-propylene)-styrene, styrene-poly(ethylene-butylene)-styrene, (polystyrene/poly(ethylene-butylene)/polystyrene, poly(styrene/ethylene-butylene/styrene) and the like.

Useful elastomeric resins include block copolymers having the general formula A-B-A' or A-B, where A and A' are each a thermoplastic polymer endblock which contains a styrenic moiety such as a poly(vinyl arene) and where B is an elastomeric polymer midblock such as a conjugated diene or a lower alkene polymer. Block copolymers of the A-B-A' type can have different or the same thermoplastic block polymers for the A and A' blocks, and the present block copolymers are intended to embrace linear, branched and radial block copolymers. In this regard, the radial block copolymers may be designated (A-B)$_m$—X, wherein X is a polyfunctional atom or molecule and in which each (A-B)$_m$-radiates from X in a way that A is an endblock. In the radial block copolymer, X may be an organic or inorganic polyfunctional atom or molecule and m is an integer having the same value as the functional group originally present in X. It is usually at least 3, and is frequently 4 or 5, but not limited thereto. Thus, in the present invention, the expression "block copolymer", and particularly "A-B-A'" and "A-B" block copolymer, is intended to embrace all block copolymers having such rubbery blocks and thermoplastic blocks as discussed above, which can be extruded (e.g., by meltblowing), and without limitation as to the number of blocks. Commercial examples of such elastomeric copolymers are, for example, those known as KRATON® materials which are available from Shell Chemical CoMPany of Houston, Tex. KRATON® block copolymers are available in several different formulations, a number of which are identified in U.S. Pat. Nos. 4,663,220, 4,323,534, 4,834,738, 5,093,422 and 5,304,599, hereby incorporated by reference.

Polymers composed of an elastomeric A-B-A-B tetrablock copolymer may also be used in the practice of this invention. Such polymers are discussed in U.S. Pat. No. 5,332,613 to Taylor et al. In such polymers, A is a thermoplastic polymer block and B is an isoprene monomer unit hydrogenated to a substantially a poly(ethylene-propylene) monomer unit. An example of such a tetrablock copolymer is a styrene-poly(ethylene-propylene)-styrene-poly (ethylene-propylene) or SEPSEP elastomeric block copolymer available from the Shell Chemical Company of Houston, Tex. under the trade designation KRATON® G-1657.

Other exemplary elastomeric materials which may be used include polyurethane elastomeric materials such as, for example, those available under the trademark ESTANE® from B. F. Goodrich & Co. or MORTHANE® from Morton Thiokol Corp., polyester elastomeric materials such as, for example, those available under the trade designation HYTREL® from E. I. DuPont De Nemours & Company, and those known as ARNITEL®, formerly available from Akzo Plastics of Arnhem, Holland and now available from DSM of Sittard, Holland.

Another suitable material is a polyester block amide copolymer having the formula:

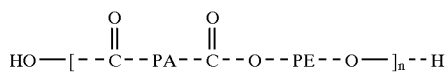

where n is a positive integer, PA represents a polyamide polymer segment and PE represents a polyether polymer segment In particular, the polyether block amide copolymer has a melting point of from about 150° C. to about 170° C., as measured in accordance with ASTM D-789; a melt index of from about 6 grams per 10 minutes to about 25 grams per 10 minutes, as measured in accordance with ASTM D-1238, condition Q (235 C/1 Kg load); a modulus of elasticity in flexure of from about 20 Mpa to about 200 MPa, as measured in accordance with ASTM D-790; a tensile strength at break of from about 29 Mpa to about 33 MPa as measured in accordance with ASTM D-638 and an ultimate elongation at break of from about 500 percent to about 700 percent as measured by ASTM D-638. A particular embodiment of the polyether block amide copolymer has a melting point of about 152° C. as measured in accordance with ASTM D-789; a melt index of about 7 grams per 10 minutes, as measured in accordance with ASTM D-1238, condition Q (235 C/1 Kg load); a modulus of elasticity in flexure of about 29.50 MPa, as measured in accordance with ASTM D-790; a tensile strength at break of about 29 MPa, a measured in accordance with ASTM D-639; and an elongation at break of about 650 percent as measured in accordance with ASTM D-638. Such materials are available in various grades under the trade designation PEBAX® from ELF Atochem Inc. of Glen Rock, N.J. Examples of the use of such polymers may be found in U.S. Pat. Nos. 4,724,184, 4,820,572 and 4,923,742 hereby incorporated by reference, to Killian et al. and assigned to the same assignee as this invention.

Elastomeric polymers also include copolymers of ethylene and at least one vinyl monomer such as, for example, vinyl acetates, unsaturated aliphatic monocarboxylic acids, and esters of such monocarboxylic acids. The elastomeric copolymers are disclosed in, for example, U.S. Pat. No. 4,803,117.

The thermoplastic copolyester elastomers include copolyetheresters having the general formula:

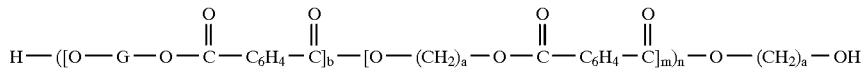

where "G" is selected from the group consisting of poly(oxyethylene)-alpha,omega-diol, poly(oxypropylene)-alpha, omega-diol, poly(oxytetramethylene)-alpha,omega-diol and "a" and "b" are positive integers including 2, 4 and 6, "m" and "n" are positive integers including 1–20. Such materials generally have an elongation at break of from about 600 percent to 750 percent when measured in accordance with ASTM D-638 and a melt point of from about 350° F. to about 400° F. (176 to 205° C.) when measured in accordance with ASTM D-2117.

Commercial examples of such copolyester materials are, for example, those known as ARNITEL®, formerly available from Akzo Plastics of Arnhem, Holland and now available from DSM of Sittard, Holland, or those known as HYTREL® which are available from E.I. duPont de Nemours of Wilmington, Del. Polyester elastomeric materials are disclosed in, for example, U.S. Pat. No. 4,741,949 to Morman et al. and U.S. Pat. No. 4,707,398 to Boggs, hereby incorporated by reference.

In addition to the polyolefin resin, the film of the present inventions also includes a filler which enables development of micropores during orientation of the film. As used herein a "filler" is meant to include particulates and other forms of materials which can be added to the polymer and which will not chemically interfere with or adversely affect the extruded film but is able to be uniformly dispersed throughout the film. Preferably, the filler particles are essentially non-spherical in shape. In one embodiment, the filler particles may be ground calcium carbonate and have an mean aspect ratio (e.g.: ratio of length to height of particle) of at least about 1.5 to 1. Preferably, the filler include particulates with mean particle sizes in the range of about 0.9 to about 1.3 microns, wherein 98% of the filler particles have a particle size of less than about 8 microns. As used herein, the term "particle size" describes the largest diameter or length of a filler particle. The film will include at least about 40 percent(%) filler based upon the total weight of the film. In an application such as the personal care products, the film preferably at least about 60% by weight filler. The preferred filler content for an application such as medical or surgical care and industrial workwear at least about 65% by weight filler. Both organic and inorganic fillers are contemplated to be within the scope of the present invention provided that they do not interfere with the film formation process, the breathability of the resultant film or its ability to bond to another layer such as a fibrous polyolefin nonwoven web. Examples of suitable fillers include calcium carbonate ($CaCO_3$), various kinds of clay, silica ($SiO_2$), alumina, barium sulfate, sodium carbonate, talc, magnesium sulfate, titanium dioxide, zeolites, aluminum sulfate, cellulose-type powders, diatomaceous earth, magnesium sulfate, magnesium carbonate, barium carbonate, kaolin, mica, carbon, calcium oxide, magnesium oxide, aluminum hydroxide, pulp powder, wood powder, cellulose derivative, polymer particles, chitin and chitin derivatives. The filler particles are preferably coated with a fatty acid, such as stearic acid, or a larger chain fatty acid then starch such as behenic acid, which may facilitate the free flow of the particles (in bulk) and their ease of dispersion into the polymer matrix.

Generally, it has been possible to produce films with a water vapor transmission rate (WVTR) of at least about 300 grams per square meter per 24 hours, measured by test procedure a modified ASTM Test Method E96-80, using CELGARD® 2500 as control. In general, factors that affect the amount of breathability include the amount of filler, the film stretching conditions (e.g., whether it is performed at cold, ambient or elevated temperatures), draw ratio, and film thickness. Preferably, the WVTR of the film of the present invention that may be used as a component in a limited-use or disposable item is from about 1,200 to about 2,220 g/m²/24 hrs. for applications such as personal care, where it is desirable that the film surface opposite the contaminant source remains dry to the touch. The preferred film has a WVTR of at least about 3,500 g/m²/24 hrs. for applications such as surgical and health care as well as disposable workwear. In addition, the preferred films of the present invention are elastic in nature.

The term "elastic" is used herein to mean any material which, upon application of a biasing force, is stretchable, that is, elongatable, to a stretched, biased length which is at least about 150 percent of its relaxed unbiased length, and which will recover at least 50 percent of its elongation upon release of the stretching, elongating force. A hypothetical example would be a one (1) inch sample of a material which is elongatable to at least 1.50 inches and which, upon being elongated to 1.50 inches and released, will recover to a length of not more than 1.25 inches. Many elastic materials may be stretched by much more than 50 percent of their relaxed length, for example, 100 percent or more, and many of these will recover to substantially their original relaxed length, for example, to within 105 percent of their original relaxed length, upon release of the stretching force.

As used herein, the term "nonelastic" refers to any material which does not fall within the definition of "elastic," above.

These properties can be obtained by first preparing a polyolefin resin of a propylene-based polymer including atactic polypropylene units, filling (mixing) the resin with filler, extruding a film from the filled resin and thereafter preferably cold-stretching or orienting the filled film in at least one direction, usually, the machine direction. As explained in greater detail below, the resultant film is microporous and has increased strength properties in the transverse or cross-machine direction.

Processes for forming filled films and orienting them are well-known to those skilled in the art. In general, a process for forming filled film 10 is shown in FIG. 1 of the drawings. Referring to the figure, filled film 10 is formed from a film extrusion apparatus 40 such as a cast or blown unit which could be in-line or off-line. Typically the apparatus 40 will include an extruder 41. Filled resin including the polymeric material and filler is prepared in a mixer 43 and directed to the extruder 41. The film 10 is extruded into a pair of nip or chill rollers 42 one of which may be patterned so as to iMPart an embossed pattern to the newly formed film 10.

From the film extrusion apparatus 40 or off line rolls supplied, the filled film 10 is directed to a film stretching unit 44 such as a machine direction orienter, which is a commercially available device from vendors such as the Marshall and Williams CoMPany of Providence, Rhode Island. Such an apparatus 44 has a plurality of stretching rollers 46 moving at progressively faster speeds relative to the pair disposed before it. Optionally, the speed of the rollers may vary in a step function where a set the rollers run at a higher speed then a second set of rollers. These rollers 46 apply an amount stress and thereby progressively stretch filled film 10 to a stretch length in the machine direction of the film which is the direction of travel of filled film 10 through the process as shown in FIG. 1.

Advantageously, the film of the present invention requires a preferred draw ratio of about 3:1. The preferred stretch temperature is about 170° F. Alternatively, the stretch rollers 46 may orient the film in a cold stretching process.

The term "cold stretching" as used herein is defined as stretching or drawing a film, or film portion or product, to greater than its original length and at a stretching temperature, i.e., the temperature of the film being stretched, less than the temperature at which melting begins when the film is uniformly heated from a temperature of about 25° C. per minute. As is known to those skilled in the art, the temperature at which melting begins and the fusion temperature may be determined by a standard differential thermal analyzer (DTA), or by other known apparatus which can detect thermal transitions of a polymer.

The temperature at which melting begins varies with the type of polymer, the molecular weight distribution of the polymer, and the crystalline morphology of the film. For example, a film made of a polypropylene material having a melting point of 158° C. may be cold stretched at a temperature below about 120° C., preferably between about 10° C. and 70° C., and conveniently at ambient temperature, e.g. 25° C.

At the stretched length, a plurality of micropores form in the film 10. If desired, film 10 is directed out of apparatus 44 so that the stress is removed to allow the stretched film 10 to relax.

Figures 2, 3:
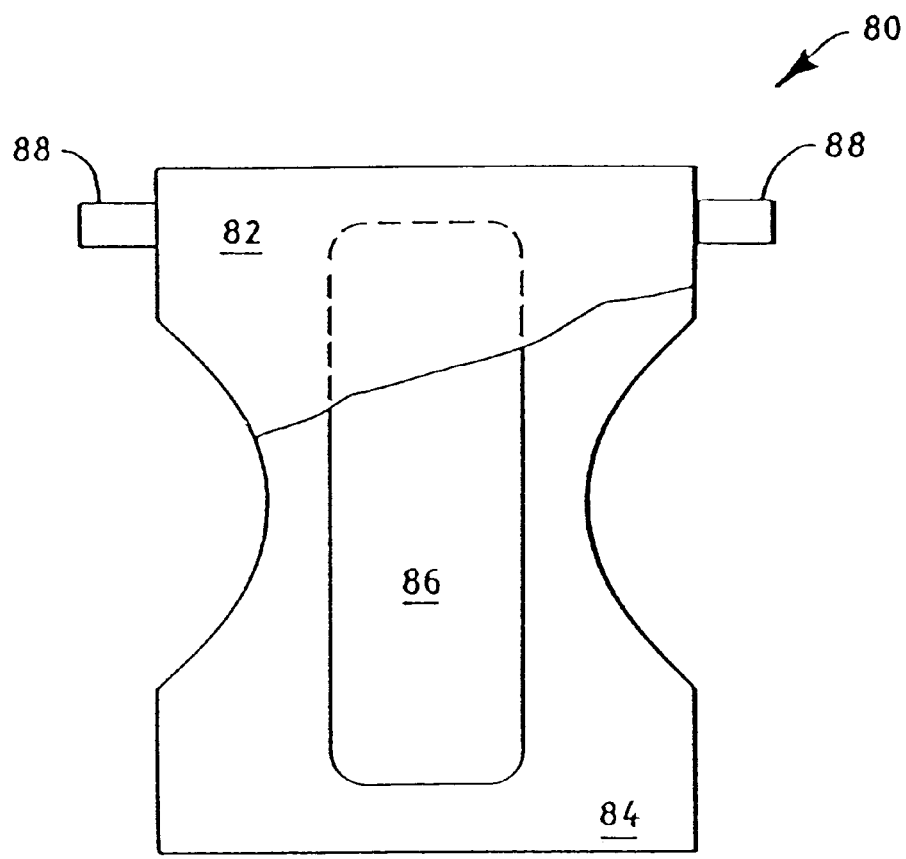
FIG. 2 is a cross-section side view of a film/nonwoven laminate according to the present invention.
FIG. 3 is a partially cut away top plan view of an exemplary personal care absorbent article, in this case a diaper, which may utilize a film made according to the present invention.

Oftentimes it may be desirable to laminate filled film 10 to one or more substrates or support layers 20 such as is shown in FIG. 2. Lamination of film may enhance the strength and thus durability of the film. If desired, filled film 10 may be attached to one or more support layers 30 to form a laminate 32. Referring again to FIG. 1, a conventional fibrous nonwoven web forming apparatus 48, such as a pair of spunbond machines, is used to form the support layer 30. The long, essentially continuous fibers 50 are deposited onto a forming wire 52 as an unbonded web 54 and the unbonded web 54 is then sent through a pair of bonding rolls 56 to bond the fibers together and increase the tear strength of the resultant web support layer 30. One or both of the rolls are often heated to aid in bonding. Typically, one of the rolls 56 is also patterned so as to impart a discrete bond pattern with a prescribed bond surface area to the web 30. The other roll is usually a smooth anvil roll but this roll also may be patterned if so desired. Once filled film 10 has been sufficiently stretched and the support layer 30 has been formed, the two layers are brought together and laminated to one another using a pair of laminating rolls or other means 58. As with the bonding rolls 56, the laminating rolls 58 may be heated. Also, at least one of the rolls may be patterned to create a discrete bond pattern with a prescribed bond surface area for the resultant laminate 32. Generally, the maximum bond point surface area for a given area of surface on one side of the laminate 32 will not exceed about 50 percent of the total surface area. There are a number of discrete bond patterns which may be used. See, for example, Brock et al., U.S. Pat. No. 4,041,203 which is incorporated herein by reference in its entirety Once the laminate 32 exists the laminating rolls 58, it may be wound up into a roll 60 for subsequent processing Alternatively, the laminate 32 may continue in-line for further processing or conversion.

While the support layers 30 and film 10 shown in FIG. 1 were bonded together through thermal point bonding, other bonding means can also be used. Suitable alternatives include, for example, adhesive bonding and the use of tackifiers. In adhesive bonding, an adhesive such as a hot melt adhesive is applied between the film and fiber to bind the film and fiber together. The adhesive can be applied by, for example, melt spraying, printing or meltblowing. Various types of adhesives are available, including those produced from amorphous polyalphaolefins, ethylene vinyl acetate-based hot melts, and Kraton® brand adhesives available from Shell Chemical of Houston, Tex. and Rextac™ Brand Adhesives from Rexene of Odessa, Tex.

When the film and support layer(s) is bonded with tackifiers, the tackifier may be incorporated into the film itself. The tackifier essentially serves to increase adhesion between the film and fiber layers. The film and fiber laminate may subsequently be thermally point-bonded, although generally very little heat is required since the tackifier tends to increase the pressure sensitivity of the film and a bond somewhat like and adhesive bond can be formed. Examples of useful tackifiers include Wingtack™ 95, available from Goodyear Tire & Rubber Co. of Akron, Ohio, and Escorez™ 5300, available from Exxon Chemical CoMPany of Houston, Tex.

The direction of elasticity in the laminate may be tailored by the state of the film, ie., whether it is relaxed or stretched, during the bonding with the support layer, as well as the physical property of the support layer material. For example, if the film is relaxed prior to bonding and the support layer is extensible in the cross-machine direction ("CD"), then a laminate with both CD and machine-direction ("MD") stretch can be produced. Additionally, if the film is bonded to a non-extensible in the CD direction support layer while in a stretched state, then a laminate with a MD stretch can be produced.

The support layers 30 as shown in FIG. 2 are fibrous nonwoven webs. The manufacture of such fibrous nonwoven webs is known. Such fibrous nonwoven webs can add additional properties to filled film 10, such as a more soft, cloth-like feel. This is particularly advantageous when filled film 10 is being used as a barrier layer to liquids in such applications as outer covers for personal care absorbent articles and as barrier materials for hospital, surgical, and clean room applications such as, for example, surgical drapes, gowns and other forms of apparel. Attachment of the support layers 30 to the filled film 10 may be by the use of a separate adhesive such as hot-melt and solvent based adhesives or through the use of heat and/or pressure (also known as thermal bonding) as with heated bonding rolls. The adhesive or thermal means may be applied continuously between the layers (continuous bonding), or at discrete portion of the layers (point-bonding).

The support layer in a laminate containing the film layer of the present invention can be necked polypropylene spunbond, crimped polypropylene spunbond, bonded carded webs, elastomeric spunbond or meltblown fabrics produced from elastomeric resins. A particularly advantageous support layer is a fibrous nonwoven web. Such webs may be formed from a number of processes including, but not limited to, spunbonding, meltblowing and bonded carded web processes. Meltblown fibers are formed by extruding molten thermoplastic material through a plurality of fine, usually circular, capillaries as molten threads or filaments into a high velocity usually heated gas stream such as air, which attenuates the filaments of molten thermoplastic material to reduce their diameters. Thereafter, the meltblown fibers are carried by the high velocity usually heated gas stream and are deposited on a collecting surface to form a web of randomly dispersed meltblown fibers. The meltblown process is well-known and is described in various patents and publications, including NRL Report 4364, "Manufacture of Super-Fine Organic Fibers" by B. A. Wendt, E. L. Boone and D. D. Fluharty; NRL Report 5265, "An Improved Device For The Formation of Super-Fine Thermoplastic Fibers" by K. D. Lawrence, R. T. Lukas, J. A. Young; U.S. Pat. No. 3,676,242, issued Jul. 11, 1972, to Prentice; and U.S. Pat. No. 3,849,241, issued Nov. 19, 1974, to Buntin, et al. The foregoing references are incorporated herein by reference in their entirety.

Spunbond fibers are formed by extruding a molten thermoplastic material as filaments from a plurality of fine, usually circular, capillaries in a spinnerette with the diameter of the extruded filaments then being rapidly reduced, for example, by non-educative or educative fluid-drawing or other well-known spunbonding mechanisms. The production of spunbond nonwoven webs is illustrated in patents such as Appel et al., U.S. Pat. No. 4,340,563; Matsuki, et al., U.S. Pat. No. 3,802,817; Dorschner et al., U.S. Pat. No. 3,692,618; Kinney, U.S. Pat. Nos. 3,338,992 and 3,341,394; Levy, U.S. Pat. No. 3,276,944; Peterson, U.S. Pat. No. 3,502,538; Hartman, U.S. Pat. No. 3,502,763; Dobo et al., U.S. Pat. No. 3,542,615; and Harmon, Canadian Patent No. 803,714. All of the foregoing references are incorporated herein by reference in their entirety.

A plurality of support layers 30 also may be used. Examples of such materials can include, for example, spunbond/meltblown laminates and spunbond/meltblown/spunbond laminates such as are taught in Brock et al., U.S. Pat. No. 4,041,203 which is incorporated herein by reference in its entirety.

Bonded carded webs are made from staple fibers which are usually purchased in bales. The bales are placed in a picker which separates the fibers. Next the fibers are sent through a combing or carding unit which further breaks apart and aligns the staple fibers in the machine direction so as to form a machine direction-oriented fibrous nonwoven web. Once the web has been formed, it is then bonded by one or more of several bonding methods. One bonding method is powder bonding wherein a powdered adhesive is distributed throughout the web and then activated, usually by heating the web and adhesive with hot air. Another bonding method is pattern bonding wherein heated calender rolls or ultrasonic bonding equipment is used to bond the fibers together, usually in a localized bond pattern though the web can be bonded across its entire surface if so desired. When using bicomponent staple fibers, through-air bonding equipment is, for many applications, especially advantageous.

The process shown in FIG. 1 also may be used to create a three layer laminate. The only modification to the previously described process is to feed a supply 62 of a second fibrous nonwoven web support layer 30a into the laminating rolls 58 on a side of filled film 10 opposite that of the other fibrous nonwoven web support layer 30. As shown in FIG. 1, one or both of the support layers may be formed directly in-line, as is support layer 30. Alternatively, the supply of one or both support layers may be in the form of a pre-formed roll 62, as is support layer 30a. In either event, the second support layer 30a is fed into the laminating rolls 58 and is laminated to filled film 10 in the same fashion as the first support layer 30.

As has been stated previously, filled film 10 and the breathable laminate 32 may be used in a wide variety of applications not the least of which includes personal care absorbent articles such as diapers, training pants, incontinence devices and feminine hygiene products such as sanitary napkins. An exemplary article 80, in this case a diaper, is shown in FIG. 3 of the drawings. Referring to FIG. 3, most such personal care absorbent articles 80 include a liquid permeable top sheet or liner 82, a back sheet or outercover 84 and an absorbent core 86 disposed between and contained by the top sheet 82 and back sheet 84. Articles 80 such as diapers may also include some type of fastening means 88 such as adhesive fastening tapes or mechanical hook and loop type fasteners to maintain the garment in place on the wearer. The fastening system may contain stretch material to form "stretched ears" for greater control.

Filled film 10 by itself or in other forms such as the film/support layer laminate 32 may be used to form various portions of the article including, but not limited to, stretched ear, the top and the back sheet 84. If the film or laminate is to be used as the liner 82, it will most likely have to be apertured or otherwise made to be liquid permeable. When using a film/nonwoven laminate as the outercover 84, it is usually advantageous to place the nonwoven side facing out away from the user. In addition, in such embodiments it may be possible to utilize the nonwoven portion of the laminate as the loop portion of the hook and loop combination.

Other uses for the filled film and breathable film/support layer laminates according to the present invention include, but are not limited to, surgical drapes and gowns, wipers, barrier materials and articles of clothing or portions thereof including such items as workwear and lab coats.

The stretch parameters of the present invention (i.e., lower draw ratio) result in a film with superior transverse strength properties than conventional films that are processed at higher draw ratios. Moreover, the preferred films and laminates of the present invention, when used in an application such as medical protective garment or surgical drape, results in a durable and low-gauge product that prevents passage of undesirable microorganisms.

The advantages and other characteristics of the present invention are best illustrated by the following example:

EXAMPLE 1

Film and laminate samples having the composition listed in Table I below were prepared for evaluation.

TABLE I

| SAMPLE | SAMPLE TYPE | COMPONENTS (wt %) |
|---|---|---|
| A | Blown Monolayer Film | 65% ECC Supercoat ™[3]<br>15% Rexene Rexflex ™ D1700 (homopolymer, 0.89 g/cc (D1505 ASTM test method); 1.8 MFR[1], 158° C. melting point)<br>15% SHELL 6D81 (random polypropylene copolymer with 5.5% ethylene content (C2), 5 MFR[1])<br>5% Dow 4012 (0.916 g/cc, 12 MI[2]LDPE) |
| B | Blown Monolayer Film | 65% ECC Supercoa ™[3]<br>15% Himont X11395-5-1 (5 MFR[1])<br>15% Shell 6D82 (7 MFR[1], 5% ethylene content)<br>5% Dow 4012 (0.916 g/cc, 12 MI[2]LDPE) |
| C | Blown Monolayer Film | 65% ECC Supercoat ™[3]<br>10% Himont X11395-5-1 (5 MFR[1])<br>10% Quantum TPO TP4300HR (11 MFR[1])<br>10% Shell 6D82 (7 MFR[1], 5% ethylene content)<br>5% Dow 4012 (0.916 g/cc, 12 MI[2]LDPE) |
| D | Blown Monolayer Film | 65% CaCO$_3$ coated with behenic acid (with 0.9–1.3 mean particle size)<br>18% Himont KS059P (10 MFR[1])<br>12% Shell 6D81 (5 MFR[1], 5% ethylene content)<br>5% Colortech 10608-07<br>    98% Novacor LE0520A (LDPE 4.5 MI[2], 0.92d, tubular)<br>    2% Irgafos 168 |
| E | Blown Monolayer Film | 95% Resin Mix<br>    68% CaCO$_3$ coated with behenic acid (with 0.9–1.3 mean particle size)<br>    19% Himont K5059P (10 MFR[1])<br>    13% Shell 6D81 (5.59% ethylene content, 5 MFR[1]RCP)<br>5% Novacor LE0520A (4.5 MI[2], 0.92d, tubular) |
| F | Blown Monolayer Film | SKIN<br><br>33% Himont KS059P<br>60% Exxon 760.36 (28% V.A., 2–3 MI)<br>20% Superfloss<br>CORE<br><br>65% CaCO$_3$ coated with behenic acid (with 0.9–1.3 mean particle size)<br>18% Quantum TP4300HR (11 MFR[1])<br>12% Shell 6D81 (5 MFR, 5% ethylene content)<br>5% Colortech 10608-07<br>    98% Novacor LE0520A (LDPE 4.5 MI[2], 0.92d, tubular)<br>    2% Irgafos 168 |
| G | Cast Laminate | SKIN<br><br>33% Himont KS059P<br>60% Exxon 760.36 (28% V.A., 2–3 MI[2])<br>20% Superfloss |

TABLE I-continued

| SAMPLE | SAMPLE TYPE | COMPONENTS (wt %) |
|---|---|---|
| | | CORE |
| | | 65% CaCO$_3$ coated with behenic acid (with 0.9–1.3 mean particle size)<br>18% Himont KS059P (10 MFR$^1$)<br>12% Shell 6D81 (5 MFR$^1$, 5% C2)<br>  5% Colortech 10608-07<br>    98% Novacor LE0520A (LDPE 4.5 MI$^2$, 0.92d, tubular)<br>    2% Irgafos 168 |
| H | Cast Laminate | SKIN |
| | | 33% Himont KS059P<br>60% Exxon 760.36 (28% V.A., 2–3 MI)<br>20% Superfloss |
| | | CORE |
| | | 65% ECC Supercoat ™<br>10% Himont X11395-5-1 (5 MFR$^1$)<br>10% Quantum TPO TP4300HR (11 MFR$^1$)<br>10% Shell 6D82 (7 MFR$^1$, 5% C2)<br>  5% Dow 4012 (0.916 g/cc, 12 MI$^2$LDPE) |

$^1$MFR = melt flow rate measured at 230° C.
$^2$MI = melt index measured at 180° C.
$^3$ECC Supercoat ™ = CaCo$_3$ coated with stearic acid (with mean particle size at 0.9 to 1.3 micron) available from English China Clay of Rosell Georgia.

Each of the blown monolayer films and cast laminates were point-bonded to a non-woven to form a spunbound/film or cast laminate/spunbond laminate structure in accordance to the lamination procedure described below. All laminates were stretched in accordance to the stretch procedure described below and evaluated in accordance to the test procedures described below. Results of these tests are listed in Table II below.

LAMINATION OF FILM

Laminates were constructed with each of the monolayer film or cast laminate and blue 0.6 ounce per square yard ("OSY")random copolymer polypropylene (with 3% ethylene content) and Larostat (internal antistatic treatment) spunbond. The laminate structure was spunbond/film/spunbond. Spunbond was blue by using 0.4% SCC 11111 and 3% AMPacet 41438 (50% TiO$_2$ loaded). A Ramisch pattern roll, with a wire weave pattern, heated to a temperature of 250° F. and an anvil roller heated to 190° F. were used to bond the layers together.

STRETCHING OF LAMINATES

The point-bonded laminates from films A-E and the cast laminates F-G were stretched with a Crown MDO machine with three S-wrap rolls, available from Marshall & Williams. The laminates were preheated, stretched, and annealed at the temperatures shown in Table II (and, for Example 2, Table IV) below. The draw ratios for each laminate are also listed in Table II (and, for Example 2, Table IV) below.

PEEL TESTING

In peel or delamination testing, the point-bonded film or cast laminate was tested for the amount of tensile force which will pull the layers of the laminate apart.

Values for peel strength were obtained using a fabric with a width of 4 inches (102 mm), a clamp width of 4 inches and a constant rate of extension of 300 mm per minute. The film side of the specimen was covered with masking tape or some other suitable material in order to prevent the film from ripping apart during the test. The masking tape is on only one side of the laminate and so does not contribute to the peel strength of the sample. The sample was delaminated by hand a sufficient amount to allow it to be clamped into position. The specimen was clamped in an Sintech 2/S, available from Sintech, Inc. of Cary, N.C., which has 4 inch (102 mm) long parallel clamps. The sample specimen was then pulled apart at 180° of separation and the peel strength was recorded in grams.

TENSILE TEST

The transverse strain peak of the laminates (measured in grams) and elongation at peak load (measured in %)) were determined in accordance with Method 5102 Federal Test Methods Standard Number 191A. Sample sizes were three inch by six inches (2.54 cm×15.24 cm) with the cross machine direction of the sample running parallel to the six inch length of the sample. Five samples were run for each material and the values were averaged. The jaws of the tensile tester were three inches wide, the initial gap or gauge length was three inches (7.62 cm) and the crosshead speed was 12 inches per minute (305 mm/min).

WATER VAPOR TRANSMISSION RATE (WVTR) MEASUREMENT

The WVTR values of the monolayer film sample and the film of each laminate sample were measured in accordance with the test procedure a modified ASTM Standard Test Method Z96-80, using CELGARD® 2500 as control. Circular samples measuring three inches in diameter were cut from each of the test materials and a control which was a piece of CELGARD® 2500 film from Hoechst Celanese Corporation of Sommerville, N.J. CELGARD® 2500 film is a microporous polypropylene film. Three samples were prepared for each material. The test dish was a number 60-1 Vapometer pan distributed by Thwing-Albert Instrument CoMPany of Philadelphia, Pa. One hundred milliliters of water were poured into each Vapometer pan and individual samples of the test materials and control material were placed across the open tops of the individual pans. Screw-on flanges were tightened to form a seal along the edges of the pan, leaving the associated test material or control material exposed to the ambient atmosphere over a 6.5 centimeter diameter circle having an exposed area of approximately 33.17 square centimeters. The pans were weighed and then placed in a forced air oven at 100° F. (32° C.) for 24 hours.

The oven was a constant temperature oven with external air circulating through it to prevent water vapor accumulation inside. A suitable forced air oven is, for example, a Blue M Power-O-Matic 60 oven distributed by Blue M Electric CoMPany of Blue Island, Ill. After 24 hours, the pans were removed from the oven and weighed again. The preliminary test water vapor transmission rate values were calculated with Equation (I) below:

$$\text{Test WVTR} = (\text{grams weight loss over 24 hours}) \times 315.5 \text{ g/m}^2/24 \text{ hrs} \quad (I)$$

The relative humidity within the oven was not specifically controlled.

Under predetermined set conditions of 100° F. (32° C.) and ambient relative humidity, the WVTR for the CELGARD® 2500 control has been defined to be 5000 grams per square meter for 24 hours. Accordingly, the control sample was run with each test and the preliminary test values were corrected to set conditions using equation II below:

$$\text{WVTR} = (\text{Test WVTR/control WVTR}) \times (5000 \text{ g/m}^2/24 \text{ hrs.}) \quad (II)$$

Data in Table II above shows that the laminate of the present invention, film sample A, after being oriented with a draw ratio of 3:1, has a WVTR value that is coMParable to laminate oriented at higher draw ratios (samples B–E).

Moreover, the laminate of the present invention had superior transverse strength properties than any of the laminate samples.

EXAMPLE 2

Blown film samples having the composition listed in Table III below were prepared for evaluation.

TABLE II

| | | PROCESS TEMPERATURES | | | | FILM ONLY | | |
| | | γ° σΔ | | FINAL | | Tensile Testing[3] | | |
| LAMINATE | BUR[3] | (preheat/ stretch/ anneal | DRAW RATIO | BASIS WEIGHT (g/m$^2$) | PEEL STRENGTH[2] (g) | PEAK CD STRENGTH (g/m$^2$) | PEAK (%) MD Elongation | WVTR[4] (g/m$^2$/ 24 hrs) |
|---|---|---|---|---|---|---|---|---|
| A | 1.6 | 205/195/230 | 3.00 | 23 | 82 | 922 | 263 | 4163 |
| B | 1.6 | 205/195/230 | 4.00 | 17 | 75 | 362 | 120 | 4261 |
| C | 1.6 | 205/195/230 | 3.75 | 18 | 94 | 548 | 176 | 4690 |
| D | 1.6 | 205/195/230 | 3.75 | 17 | 87 | 374 | 146 | 4347 |
| E | 1.6 | 205/200/235 | 3.75 | 35 | 91 | 462 | 95 | 3965 |
| F | NA | 200/190/220 | 3.40 | 22 | 186 | 651 | 108 | 2195 |
| G | NA | 200/190/220 | 3.75 | 21 | 137 | 452 | 113 | 2284 |
| H | NA | 200/190/220 | 3.40 | 18 | 190 | 639 | 173 | 2512 |

[3]BUR = blow up ratio, expressed in X = 1, where x is the number shown.

TABLE III

| SAMPLE | BUR | COMPONENTS (wt %) |
|---|---|---|
| W | 1.80 | 64% CaCO$_3$ coated with behenic acid (with 0.9 to 1.3 mean particle size) 12% Shell 6D82 (7 MFR, 5.5% ethylene content) 17% Rexene Rexflex ™ D1710 (10 MFR) (29.1% crystallinity) 7% Shell Kraton G1659X 2000 ppm Ciba Geigy Blend B900 |
| X | 1.75 | 64% CaCO$_3$ coated with behenic acid (with 0.9 to 1.3 mean particle size) 9% Shell 6D82 (7 mfr, 5.5% ethylene content) 27% Rexene RexFlex ™ D1700 (1.8 MFR) (29.1% crystallinity) 2000 ppm Ciba Geigy Blend B900 |
| Y | 1.85 | 64% CaCO$_3$ coated with behenic acid (with 0.9 to 1.3 mean particle size) 9% Shell 6D82 (7 MFR, 5.5% ethylene content) 27% Rexene Rexflex ™ D2300 (2 MFR) (13.9% crystallinity) 2000 Ciba Geigy Blend B900 |
| Z | 1.80 | 64% CaCO$_3$ coated with behenic acid (with 0.9 to 1.3 mean particle size) 21% Shell 6D82 (7 MFR, 5.5% ethylene content) 10% Himont X11395-5-1 (5 MFR Catalloy ™) 5% Himont KS059P (10 MFR Catalloy ™) 2000 ppm Ciba Geigy Blend B900 |

A first set of films (W1, X1, Y1 and Z1) were stretched in accordance to the stretch procedure described in Example 1 and evaluated for tensile strength in accordance to the procedure described in Example 1 above A second set of films (W2, X2, Y2 and Z2) were thermally point-bonded to a 0.6 osy random copolymer in accordance to the lamination procedure described in Example 1 above. The laminated set were then stretched, using the same process parameters as for the first set of films. The peel strength for the laminates were then measured in accordance to the testing procedure described in Example 1 above. WVTR measurements were performed for the films and laminates in accordance to the procedure described in Example 1 above. Results of evaluation on films W1, X1, Y1 and Z1 are shown in Table IV below. Results of evaluation on films W2, X2, Y2 and Z2 are shown in Table V below.

TABLE IV

| FILM | PROCESS TEMPERATURE (°F.) preheat/ stretch#1/ stretch#2/ anneal#1/ anneal#2/ | DRAW RATIO | STRETCHED BASIS WEIGHT (gm²) | Tensile Testing | | | | |
|---|---|---|---|---|---|---|---|---|
| | | | | CD PEAK LOAD (g) | MD PEAK LAOD (g) | MD ELONGATION (%) | CD ELONGATION (%) | WVTR (g/m²/24 hrs) |
| W1 | 180/180/53/53/212 | 3.50 | 23.5 | 733 | 4176 | 67 | 394 | 4258 |
| X1 | 195/195/53/53/220 | 3.00 | 28.3 | 953 | 5952 | 90 | 276 | 3552 |
| Y1 | 175/175/53/53/210 | 3.00 | 28.5 | 1158 | 5352 | 127 | 399 | 3300 |
| Z1 | 180/180/53/53/210 | 4.00 | 18.3 | 770 | 5371 | 63 | 322 | 3981 |

TABLE V

| LAMINATE | PROCESS TEMPERATURE (° F.) preheat /stretch #1 /stretch #2 /anneal #1 /anneal #2 | DRAW RATIO | STRETCHED BASIS WEIGHT (g/m²) | PEEL STRENGTH[2] (g) | WVTR (g/m²/ 24 hrs) |
|---|---|---|---|---|---|
| W2 | 180/180/53/53/212 | 3.50 | 23.5 | ?? | 3957 |
| X2 | 195/195/53/53/220 | 3.00 | 26.3 | 63 | 3572 |
| Y2 | 175/175/53/53/210 | 3.00 | 26.5 | 156 | 3301 |
| Z2 | 180/180/53/53/210 | 4.00 | 18.3 | 770 | 3547 |

The results in Tables IV further show that the films of the present invention have superior tensile properties.

EXAMPLE 3

The films having the composition listed in Table III were evaluated with a bacteriophage test, procedure ASTM F1670. Film samples (one of each for compositions W, X and Z, four for composition W) were stretched in accordance to the process conditions listed in Table VI below. The results of the bacteriophage test are also listed in Table VI.

TABLE VI

| FILM | PROCESS TEMPERATURE (° F.) preheat /stretch #1 /stretch #2 /anneal #1 /anneal #2 | DRAW RATIO | STRETCHED BASIS WEIGHT (g/m²) | BACTERIOPHAGE TEST (pass/fail) |
|---|---|---|---|---|
| W-20 | 180/180/53/53/212 | 3.50 | 23.5 | pass |
| X-20 | 195/195/53/53/220 | 3.00 | 65.3 | fail |
| Y-20 | 181/181/53/53/210 | 2.75 | 62.0 | pass |
| Y-21 | 180/180/53/53/210 | 3.00 | 62.0 | pass |

TABLE VI-continued

| FILM | PROCESS TEMPERATURE (° F.) preheat /stretch #1 /stretch #2 /anneal #1 /anneal #2 | DRAW RATIO | STRETCHED BASIS WEIGHT (g/m²) | BACTERIOPHAGE TEST (pass/fail) |
|---|---|---|---|---|
| Y-22 | 178/178/53/53/210 | 2.75 | 62.0 | pass |
| Y-23 | 175/175/53/53/210 | 3.00 | 62.0 | pass |
| Z-20 | 180/180/53/53/210 | 4.00 | 55.3 | fail |

The results of Table VI above show that films of the present invention with 64% filler (compositions W and Y of Table III) passed the bacteriophage test while RCP/Catalloy blends loaded with less (60%) filler (composition Z of Table III) failed the bacteriophage test, even though the 60% filler film has less chance of creating holes due to less filler content Moreover, the fact that a film including a flexible polyolefin (Sample X-20) failed the bacteriophage test suggests that, when selecting a flexible polyolefin for this particular application, both crystallinity content and the molecular weight (and possibly the molecular weight distribution) need to be considered.

EXAMPLE 4

Control

A control film having an overall composition of 42.3% Montell KS-084P, 39% Exxon 3445, 1% Quantum NA 334 LDPE and 16.8% Quantum 82143 was made. The formulation of the control film was as follows:

10% Skin Layer A:
  85% Montell KS-084P (polypropylene-based Catalloy)
  10% Exxon 3445 (homopolymer polypropylene)
  5% Quantum NA 334 LDPE (6MI)
80% Core Layer:
  39% KS-084P
  40% 3445
  21% Quantum 82143 (70% $TiO_2$)
10% Skin Layer B:
  35% KS-084P
  60% 3445
  5% NA 334 LDPE The control film contained a few gels with tails, but the overall quality of the film was good.

SAMPLE 1

Rexene 13S25A replaced Exxon 3445 in the core layer. When this blend entered the extrusion system, the blend contained many unmelted, but tiny, white gels. The temperature profile was adjusted higher in the core layer, which eliminated most of the gels although a few small gels remained. The resulting film also contained more gels with tails than the control.

SAMPLE 2

Shell 6D43 replaced Exxon 3445 in the core layer. The film produced by this blend had better overall dispersion of $TiO_2$ but still had a higher level than the control of gels with tails. The total frequency of gels in this film was coMParative to that of Sample 1.

SAMPLE 3

Shell WRD60-277 replaced Exxon 3445 in the core layer. The film produced with this blend was similar to Sample 2 in that the level of gels with tails was higher than that of the control. The dispersion of $TiO_2$ and the film appearance, however, were good.

SAMPLE 4

Rexene FP-D1730 replaced Montell KS-084P in the core layer. The Rexene FP-D1730 more closely matched the melting points of the other materials in the blend, as coMPared to the Catalloy because Catalloys have low melting peaks and, therefore, tend to melt first and coat the higher melting Exxon 3445 material. Again, the level of gels with tails was higher in this film than in the control. The resulting film, however, showed a noticeable improvement in the processability, as the gauge leveled out nicely and roll form improved.

SAMPLE 5

Rexene FP-D1730 replaced Montell KS-084P in the core layer and replaced Exxon 3445 in the skin layers. The resulting film contained a minimal amount of large gels and only a few small gels with tails. The processability, $TiO_2$ dispersion and appearance were very good. The film was very coMParable to the control film.

SAMPLE 6

Shell 6D43 replaced Exxon 3445 in the entire structure, i.e., in the skin layers and the core layer. This blend produced a film very similar to that in Sample 5 in terms of appearance, gel levels and roll form.

SAMPLE 7

Shell WRD60-277 replaced Exxon 3445 in the entire structure. The resulting film was very similar to the films produced in Samples 5 and 6.

SAMPLE 8

Rexene FP-D1730 replaced Montell KS-084P in all layers and Shell 6D43 replaced Exxon 3445 in all layers. The resulting film had excellent appearance. Film abnormalities such as, for example, gels, contaminants, non-dispersed pigment and carbon specs, were minimal in the unstretched film. Holes, another type of film abnormality, were not present in the unstretched or stretched film.

The control and each of the above samples were subjected to a hand stretchability test wherein the resulting films were stretched by hand. All of the blends, including the control, yielded films that showed good hand stretchability. The films produced using the blends of Samples 5–8, however, showed the best hand stretchability and were more defect tolerant. In other words, the films made using blends of Samples 5–8 could be stretched without resulting in a hole despite the presence of any film abnormalities in the film. The films of Samples 5–8 were followed by the films of Samples 1–4, which were followed by the control.

The control and Samples 5, 6 and 8 were also stretched through a machine-direction orienter under the following conditions: two preheat rolls at a temperature of 185° F., a slow stretch roll and a fast stretch roll and two anneal rolls at a temperature of 190° F. Each 0.0006 inch sample of film was stretched about 62% and retracted about 2.5% before entering the calendar. After the samples were stretched, each sample was scanned for defects, i.e., pin holes or thin spots where light comes through the stretched film, using a Fine-line Multicamera Flaw System available from Mayan Automation, Inc. at a linespeed of 600 fpm. This system can detect defects as small as 0.0148 inches in the cross machine direction. Its ability to detect defects in the machine direction is dependent upon linespeed. For example, it can detect holes as small as 0.055 inches at 300 fpm, holes as small as 0.091 inches at 500 fpm and holes as small as 0.1092 inches at 600 fpm. Table VII below shows the results of stretching test.

TABLE VII

| Film | Peak Loads (lbs.) | Peak Strain (%) | Defects/1000 feet* |
|---|---|---|---|
| Control | 5.93 | 243 | 1 |
| Sample 5 | 5.68 | 231 | 18 |
| Sample 6 | 5.28 | 305 | 3 |
| Sample 8 | 5.32 | 444 | 0 |

Peak load refers to the force required to break the film samples. Peak strain refers to the ultimate elongation, or the percentage of the original length to which each sample could be stretched before breaking. As can be seen, Sample 8 had excellent elongation properties and no defects. Sample 6 also showed good elongation and has very few defects.

EXAMPLE 5

Film samples having the composition listed in Table VIII below were prepared for evaluation.

TABLE VIII

| SAMPLE | BUR | COMPONENTS (% by wt) |
|---|---|---|
| 21 | 1.80 | 64% CaCO$_3$ coated with behenic acid (with 0.9–1.3 microns mean particle size) |
| | | 15% Shell 6D82 (7 mfr, 5.5% ethylene content) |
| | | 21% Rexene RexFlex ™-D1710 (10 MFR) |
| | | 2000 ppm Ciba Geigy Blend B900 |
| 22 | 1.75 | 64% CaCO$_3$ coated with behenic acid (with 0.9–1.3 microns mean particle size) |
| | | 15% Shell 6D82 (7 mfr, 5.5% ethylene content) |
| | | 21% Rexene RexFlex ™-D1700 (1.8 MFR) |
| | | 2000 ppm Ciba Geigy Blend B900 |
| 23 | 1.75 | 64% Chalk coated with behenic acid (6 micron) |
| | | 15% Shell 6D82 (7 mfr, 5.5% ethylene content) |
| | | 21% Rexene RexFlex ™-D1710 (10 MFR) |
| | | 2000 ppm Ciba Geigy Blend B900 |
| 24 | 1.75 | 64% Chalk coated with behenic acid (6 micron) |
| | | 15% Shell 6D82 (7 mfr, 5.5% ethylene content) |
| | | 21% Rexene RexFlex ™-D1700 (1.8 MFR) |
| | | 2000 ppm Ciba Geigy Blend B900 |
| 25 | 1.75 | 64% CaCO$_3$ coated with behenic acid (with 0.9–1.3 microns mean particle size) |
| | | 21% Rexene RexFlex ™-D1710 (10 MFR) |
| | | 15% ICP PD 7632-E7 |
| | | 2000 ppm Ciba Geigy Blend B900 |
| 26 | 1.75 | 64% CaCO$_3$ coated with behenic acid (with 0.9–1.3 microns mean particle size) |
| | | 17% Shell 6D82 (7 mfr, 5.5% ethylene content) |
| | | 21% Rexene RexFlex ™-D1700 (1.8 MFR) |
| | | 7% Shell Kraton ® G1659X |
| | | 15% ICP PD 7632-E7 |
| | | 2000 ppm Ciba Geigy Blend B900 |
| 27 | 1.80 | 64% CaCO$_3$ coated with behenic acid (with 0.9–1.3 microns mean particle size) |
| | | 12% Shell 6D82 (7 mfr, 5.5% ethylene content) |
| | | 17% Rexene RexFlex ™-D1710 (10 MFR) |
| | | 7% Shell Kraton ® G1659X |
| | | 2000 ppm Ciba Geigy Blend B900 |
| 28 | 1.80 | 64% CaCO$_3$ coated with behenic acid (with 0.9–1.3 microns mean particle size) |
| | | 21% Shell 6D82 (7 mfr, 5.5% ethylene content) |
| | | 15% Rexene RexFlex ™ D1710 (10 MFR) |
| | | 2000 ppm Ciba Geigy Blend B900 |
| 29 | 1.75 | 64% CaCO$_3$ coated with behenic acid (with 0.9–1.3 microns mean particle size) |
| | | 21% Rexene RexFlex ™ D1710 (10 MFR) |
| | | 15% Duraflex ® 8340 (4 MI) |
| | | 2000 ppm Ciba Geigy Blend B900 |
| 30 | 1.75 | 64% CaCO$_3$ coated with behenic acid (with 0.9–1.3 microns mean particle size) |
| | | 17% Shell 6D82 (7 mfr, 5.5% ethylene content) |
| | | 7% Shell Kraton ® G1659X |
| | | 12% Duraflex 8340 (4 MI) |
| | | 2000 ppm Ciba Geigy Blend B900 |
| 31 | 1.80 | 64% CaCO$_3$ coated with behenic acid (with 0.9–1.3 microns mean particle size) |
| | | 13% Shell 6D82 (7 mfr, 5.5% ethylene content) |
| | | 19% Rexene RexFlex ™-D1710 (10 MFR) |
| | | 4% Rexene RexFlex ™-D100 |
| | | 2000 ppm Ciba Geigy Blend B900 |
| 32 | 1.75 | 64% CaCO$_3$ coated with behenic acid (with 0.9–1.3 microns mean particle size) |
| | | 15% Shell 6D82 (7 mfr, 5.5% ethylene content) |
| | | 10% Rexene RexFlex ™-D1710 (10 MFR) |
| | | 4% Rexene RexFlex ™-D100 |
| | | 7% Shell Kraton ® G1659X |
| | | 2000 ppm Ciba Geigy Blend B900 |
| 33 | 1.75 | 64% CaCO$_3$ coated with behenic acid (with 0.9–1.3 microns mean particle size) |
| | | 15% Rexene RexFlex ™-D1710 (10 MFR) |
| | | 4% Rexene RexFlex ™-D100 |
| | | 7% ICP PD 7632-E7 |
| | | 10% Duraflex 8340 (4 MI) |
| | | 2000 ppm Ciba Geigy Blend B900 |
| 34 | 1.85 | 64% CaCO$_3$ coated with behenic acid (with 0.9–1.3 microns mean particle size) |
| | | 19% Shell 6D82 (7 mfr, 5.5% ethylene content) |
| | | 4% Rexene RexFlex ™-D100 |
| | | 13% Duraflex 8340 (4 MI) |
| | | 2000 ppm Ciba Geigy Blend B900 |
| 35 | 1.70 | 64% Chalk coated with behenic acid (6 micron) |
| | | 15% Shell 6D82 (7 mfr, 5.5% ethylene content) |
| | | 21% Rexene RexFlex ™-D1710 (10 MFR) |
| | | 2000 ppm Ciba Geigy Blend B900 |

TABLE VIII-continued

| SAMPLE | BUR | COMPONENTS (% by wt) |
|---|---|---|
| 36 | 1.80 | 64% Chalk coated with behenic acid (6 micron)<br>17% Shell 6D82 (7 mfr, 5.5% ethylene content)<br>12% Rexene RexFlex ™-D1710 (10 MFR)<br>7% Shell Kraton ® G1659X<br>2000 ppm Ciba Geigy Blend B900 |
| 37 | 1.70 | 64% Chalk coated with behenic acid (6 micron)<br>17% Rexene RexFlex ™-D1710 (10 MFR)<br>7% Shell Kraton ® G1659X<br>12% Duraflex 8340 (4 MI)<br>2000 ppm Ciba Geigy Blend B900 |
| 38 | 1.75 | 64% Chalk coated with behenic acid (6 micron)<br>21% Shell 6D82 (7 mfr, 5.5% ethylene content)<br>15% Duraflex 8340 (4 MI)<br>2000 ppm Ciba Geigy Blend B900 |
| 39 | 1.75 | 64% Chalk coated with behenic acid (6 micron)<br>10% Shell 6D82 (7 mfr, 5.5% ethylene content)<br>15% Rexene RexFlex ™-D1710 (10 MFR)<br>4% Rexene RexFlex ™-D100<br>7% Shell Kraton ® G1659X<br>2000 ppm Ciba Geigy Blend B900 |
| 40 | 1.70 | 64% Chalk coated with behenic acid (6 micron)<br>19% Shell 6D82 (7 mfr, 5.5% ethylene content)<br>4% Rexene RexFlex ™-D100<br>2000 ppm Ciba Geigy Blend B900 |
| 41 | 1.75 | 64% Chalk coated with behenic acid (6 micron)<br>19% Rexene RexFlex ™-D1710 (10 MFR)<br>4% Rexene RexFlex ™-D100<br>13% Duraflex 8340 (4 MI)<br>2000 ppm Ciba Geigy Blend B900 |
| 42 | 1.70 | 64% Chalk coated with behenic acid (6 micron)<br>15% Shell 6D82 (7 mfr, 5.5% ethylene content)<br>4% Rexene RexFlex ™-D100<br>7% Shell Kraton ® G1659X<br>10% Duraflex 8340 (4 MI)<br>2000 ppm Ciba Geigy Blend B900 |

The films were stretched in accordance to the stretch procedure described in Example 1 and evaluated for tensile strength in accordance to the procedure described in Example 1 above. Results are listed in Table IX below.

TABLE IX

| FILM | PROCESS TEMPERATURE (°F.)<br>preheat/stretch#1/stretch#2/anneal#1/anneal#2/ | DRAW RATIO | STRETCHED BASIS WEIGHT (g/m$^2$) | CD PEAK LOAD (g/in$^2$) | MD PEAK LOAD (g/in$^2$) | MD ELONGATION (%) | CD ELONGATION (%) | WVTR (g/m$^2$/24 hrs) |
|---|---|---|---|---|---|---|---|---|
| 21 | 185/185/53/53/210 | 3.50 | 22.5 | 623 | 5136 | 63 | 243 | 4389 |
| 22 | 195/195/53/53/220 | 3.60 | 24.3 | 1036 | 6616 | 66 | 283 | 4462 |
| 23 | 180/180/53/53/212 | 3.50 | 19.0 | 525 | 4178 | 47 | 235 | 5176 |
| 24 | 190/190/53/53/220 | 3.75 | 21.2 | 996 | 5906 | 54 | 265 | 4628 |
| 25 | | | WOULD NOT STRETCH NO SAMPLE GENERATED | | | | | |
| 26 | 205/205/53/53/220 | 3.75 | 21.0 | 796 | 6682 | 41 | 241 | 5120 |
| 27 | 180/180/53/53/212 | 3.50 | 23.5 | 733 | 4176 | 67 | 394 | 4258 |
| 28 | 180/180/53/53/212 | 3.50 | 26.3 | 1029 | 6061 | 67 | 240 | 4471 |
| 29 | 140/114/53/53/180 | 3.50 | 17.8 | 731 | 4357 | 56 | 258 | 3301 |
| 30 | 170/170/53/53/200 | 3.50 | 17.8 | 492 | 3836 | 58 | 226 | 3970 |
| 31 | 185/185/53/53/210 | 3.50 | 21.0 | 651 | 4750 | 63 | 295 | 4758 |
| 32 | 180/180/53/53/212 | 3.50 | 25.0 | 564 | 4411 | 63 | 325 | 4909 |
| 33 | 173/173/53/53/210 | 3.50 | 19.0 | 636 | 3546 | 86 | 316 | 2181 |
| 34 | 180/180/53/53/210 | 3.25 | 17.7 | 564 | 4687 | 74 | 283 | 3254 |
| 35 | 180/180/53/53/212 | 4.00 | 22.3 | 684 | 5122 | 46 | 281 | 4855 |
| 36 | 185/185/75/75/210 | 4.00 | 20.3 | 677 | 5601 | 59 | 321 | 5148 |
| 38 | 180/180/53/53/210 | 3.50 | 21.2 | 909 | 4580 | 76 | 265 | 3558 |
| 39 | 175/175/113/113/200 | 3.75 | 23.5 | 662 | 4981 | 74 | 383 | 5042 |
| 40 | 185/185/63/63/210 | 4.00 | 16.0 | 469 | 4201 | 46 | 221 | 5772 |
| 41 | 165/165/113/113/190 | 3.20 | 29.5 | 1071 | 4574 | 75 | 309 | 2427 |
| 42 | 170/170/113/113/190 | 3.50 | 18.0 | 632 | 3704 | 70 | 336 | 3976 |

The results in Tables IX further show that of the present invention have excellent tensile properties.

Therefore, the films of the present invention have high water vapor transmission rate and elasticity that iMPart a wide variety of functionalities including vapor permeability, liquid impermeability, and comfort fit and stretch Furthermore, such films can be attached to support layers to form laminates.

Of course, it should be understood that a wide range of changes and modifications can be made to the embodiments described above. It is therefore intended that the foregoing description illustrates rather than limits this invention, and that it is the following claims, including all equivalents, which define this invention.

We claim:

1. A microporous oriented film comprising:
    a polyolefin resin including a propylene-based polymer with atactic polypropylene units;
    at least about 40% by weight of the film of a filler, said filler including particles having a particle size that contributes to pore formation;
    wherein said film has a water vapor transmission rate of at least about 300 g/m$^2$/24 hours, measured by modified test procedure ASTM E-960.
2. The film of claim 1 wherein said filler particles have a fatty acid coating.
3. The film of claim 1 wherein said filler particles are generally non-spherical in shape.
4. The film of claim 1 wherein said filler particles have a mean particle size of from about 0.9 to about 1.3 microns.
5. The film of claim 1 wherein said filler particles have a mean aspect ratio of at least about 1.5:1.
6. The film of claim 1 wherein said polyolefin resin contains at least about 60% by weight filler.
7. The film of claim 1 wherein said filler is calcium carbonate.
8. The film of claim 1 wherein said polypropylene-based polymer has a crystallinity level of from about 10 to about 30% by weight of said polymer, measured by differential scanning calorimetry method.
9. The film of claim 1 wherein said polyolefin resin includes a blend of components selected from low crystallinity polypropylene random copolymers, flexible polyolefins, elastomeric copolymers and combination thereof.
10. The film of claim 9 wherein said low crystallinity polypropylene random and copolymers has an ethylene content of at least 3%.
11. The film of claim 9 wherein said polyolefin resin includes:
    from about 10 to about 80% flexible polyolefins, based upon the weight of the resin;
    up to about 75% low crystallinity polypropylene random copolymers;
    up to about 60% elastomeric copolymer.
12. A laminate comprising:
    a filled film a polyolefin resin including a polypropylene-based polymer with atactic polypropylene units and a filler in an amount of at least about 40% by weight of said filled film, said filler including particles having a particle size that contributes to pore formation, said filled film has a water vapor transmission rate of at least about 300 g/m$^2$/24 hours, measured by modified test procedure ASTM E-96; and
    at least one support layer.

* * * * *